(12) United States Patent
Batista

(10) Patent No.: US 10,638,793 B2
(45) Date of Patent: May 5, 2020

(54) AEROSOL-GENERATING SYSTEM COMPRISING MOVEABLE CARTRIDGE

(71) Applicant: Philip Morris Products S.A., Neuchatel (CH)

(72) Inventor: Rui Nuno Batista, Morges (CH)

(73) Assignee: Philip Morris Products S.A., Neuchatel (CH)

( * ) Notice: Subject to any disclaimer, the term of this patent is extended or adjusted under 35 U.S.C. 154(b) by 508 days.

(21) Appl. No.: 15/536,373

(22) PCT Filed: Dec. 14, 2015

(86) PCT No.: PCT/EP2015/079595
§ 371 (c)(1),
(2) Date: Jun. 15, 2017

(87) PCT Pub. No.: WO2016/096728
PCT Pub. Date: Jun. 23, 2016

(65) Prior Publication Data
US 2017/0360095 A1  Dec. 21, 2017

(30) Foreign Application Priority Data
Dec. 15, 2014 (EP) .................................. 14198070

(51) Int. Cl.
*A24F 47/00* (2020.01)
*A61M 15/00* (2006.01)
(Continued)

(52) U.S. Cl.
CPC ......... *A24F 47/008* (2013.01); *A61M 11/042* (2014.02); *A61M 15/0091* (2013.01);
(Continued)

(58) Field of Classification Search
None
See application file for complete search history.

(56) References Cited

U.S. PATENT DOCUMENTS 4,945,931 A  8/1990 Gori
5,666,977 A  9/1997 Higgins et al.
(Continued)

FOREIGN PATENT DOCUMENTS

| JP | 2000-257647 | 9/2000 |
|---|---|---|
| JP | 2005-34021 | 2/2005 |

(Continued)

OTHER PUBLICATIONS

Combined Chinese Office Action and Search Report dated Jul. 22, 2019 in Patent Application No. 201580064007.2 (with English translation of Categories of Cited Documents), 7 pages.
(Continued)

*Primary Examiner* — Phu H Nguyen
(74) *Attorney, Agent, or Firm* — Oblon, McClelland, Maier & Neustadt, L.L.P.

(57) ABSTRACT

An aerosol-generating system is provided, including a housing including an air inlet and an air outlet defining an air flow path therebetween; a heater element; and a cartridge moveably mounted in the housing and reversibly displaceable from a first position to a second position, the cartridge including a moveable plunger, a liquid storage portion configured to hold an aerosol-generating liquid, and an opening configured to deliver the aerosol-generating liquid, wherein the cartridge is further configured to activate release of a portion of the aerosol-generating liquid through the opening, when the cartridge is moved by an airstream created between the air inlet and the air outlet within the housing.

16 Claims, 8 Drawing Sheets

(51) Int. Cl.
*A61M 11/04* (2006.01)
*A61M 15/06* (2006.01)
*A61M 16/20* (2006.01)

(52) U.S. Cl.
CPC ........ *A61M 15/0093* (2014.02); *A61M 15/06* (2013.01); *A61M 15/0061* (2014.02); *A61M 16/207* (2014.02); *A61M 2205/0211* (2013.01); *A61M 2209/045* (2013.01)

(56) References Cited

U.S. PATENT DOCUMENTS

| | | |
|---|---|---|
| 2014/0190496 A1 | 7/2014 | Wensley et al. |
| 2014/0190501 A1 | 7/2014 | Liu |
| 2014/0355969 A1 | 12/2014 | Stern |
| 2015/0047662 A1 | 2/2015 | Hopps |

FOREIGN PATENT DOCUMENTS

| | | |
|---|---|---|
| JP | 2005-44710 | 2/2005 |
| JP | 2006-263477 | 10/2006 |
| JP | 2013-521818 | 6/2013 |
| JP | 2013-526382 | 6/2013 |
| JP | 2014-512207 | 5/2014 |
| WO | WO 2013/152873 A1 | 10/2013 |

OTHER PUBLICATIONS

International Search Report and Written Opinion dated Mar. 30, 2016 in PCT/EP2015/079595, filed Dec. 14, 2015.
English translation of Notice of Reasons for Rejection dated Dec. 25, 2019 in corresponding Japanese Patent Application No. 2017-529369, (5 pages).

AEROSOL-GENERATING SYSTEM COMPRISING MOVEABLE CARTRIDGE

The present invention relates to aerosol-generating systems comprising a cartridge for holding a liquid and a heater assembly that is suitable for vaporizing the liquid. In particular, the invention relates to handheld aerosol-generating systems, such as electrically operated aerosol-generating systems.

Electrically operated aerosol-generating systems that vaporise a liquid by heating to form an aerosol typically comprise a coil of wire that is wrapped around a capillary material that holds the liquid. Electric current passing through the wire causes resistive heating of the wire which vaporises the liquid in the capillary material. The capillary material is typically held within an airflow path so that air is drawn past the wick and entrains the vapour. The vapour subsequently cools to form an aerosol.

In addition to the conveying of the liquid from a liquid reservoir to the heater assembly, the wick also represents a closure for the cartridge such that the liquid is prevented from uncontrolled spillage out of the cartridge.

This type of system is effective at producing aerosol but it is challenging to manufacture in a low cost and repeatable way. And the wick and coil assembly, together with associated electrical connections, can be fragile and difficult to handle.

There are further drawbacks involved in wick-based vaporizing devices. The supply of liquid depends on the capillary function of the wick. If the wick becomes clogged or damaged, no or less liquid is transported to the heater hampering the aerosol generation. Thus it may be difficult to precisely define the amount of liquid to be vaporized in such wick and coil systems. In addition, in wick-based system usually a porous substrate is used in which the liquid is stored, in order to reduce the risk for leakage. However, this has the further drawback, that after consumption of the cartridge still a residual amount of liquid remains in the porous substrate which is wasted.

It would be desirable to provide a heater assembly suitable for an aerosol-generating system, such as a handheld electrically operated aerosol-generating system, that is as easy to handle as wick and coil systems, and which allows for precise determination of the amount of liquid that is to be vaporized.

In a first aspect the present invention is directed to an aerosol-generating system comprising a housing, with an air inlet and an air outlet defining an air flow channel there between, a heater element, and a cartridge moveably mounted in the housing. The cartridge is reversibly displaceable from a first position into a second position. The cartridge further comprises a liquid storage portion for holding an aerosol-generating liquid with an opening for delivery of the aerosol-generating liquid. A plunger is moveably mounted in the cartridge. When an airstream is created between the air inlet and the air outlet, the cartridge is moved by the airstream within the housing from the first position into a second position and the movement of the cartridge activates the release of a portion of the aerosol-generating liquid through the opening.

Between puffs, i.e. when no air stream is created between the air inlet and the air outlet, the cartridge is maintained in the first position in which the opening of the cartridge is blocked such that no liquid is dispensed. When, however, a user draws a puff at the aerosol-generating device the cartridge is moved into a second position in which release of the liquid is possible. Moreover the movement of the cartridge actively induces release of the liquid.

The cartridge of the present invention has the advantage that it does not require the use of porous material that absorbs the liquid, and requires no wick to convey the liquid to the heater element. Further the heater element is not necessarily an integral part of the cartridge, and therefore the heater elements needs not to be exchanged whenever the cartridge is replaced. The structure of the cartridge therefore can be manufactured at comparably low cost. Because of the small size of the opening at the release end of the cartridge, no liquid can leave the cartridge without movement of the plunger. Even if the opening of the cartridge is not pressed against the heater or a distal wall of the aerosol forming chamber, there is no risk of unintentional spillage of the liquid.

Preferably the outer cross-section of the cartridge corresponds to the inner cross-section of the housing such that the air flow channel is defined there between. The gap between the cartridge and the housing can be adjusted to a desired resistance to draw. Anti-rotation means may be provided for preventing relative rotation between the cartridge and the housing. Such anti-rotation means can consist of the cartridge and the housing having corresponding non-circular cross-sections.

The cartridge is preferably made from light-weight material, preferably from polymeric material, such that the pressure required to move the cartridge is minimized and does not depend significantly on the holding angle of the aerosol-generating system.

The opening of the liquid storage portion of the cartridge is preferably funnel-shaped. The moveable plunger preferably has a shape that corresponds to the funnel-shaped opening of the cartridge. In this way the complete liquid can be dispensed from the cartridge and after consumption of the cartridge no or only a minimum amount of residual liquid is left in the liquid storage portion of the cartridge.

The aerosol-generating system further preferably comprises a resilient element, biasing the cartridge in the first position. Further preferably the resilient element is a soft compression spring, located between the outlet end of the housing and the pressure chamber. The spring constant of the resilient member can be chosen to adopt a drawing resistance resembling the drawing resistance of conventional smoking products.

In a preferred embodiment the heater element is provided at a distal end of an aerosol forming chamber and the resilient element biases the cartridge in the first position, in which the nozzle of the cartridge is pressed against the heater element, such that liquid is prevented from being dispensed.

Preferably a self-centering structure is provided at the distal end of the aerosol forming chamber or on the heater element, wherein the nozzle of the cartridge is seated on the self-centering structure, when the cartridge is in the first position. The self-centering structure preferably has a conical portion and the release end of the nozzle has a chamfer with an angle that corresponds to the conical shape of the self-centering structure. The self-centering structure offers several advantages. Due to its shape, the self-centering structure ensures that the nozzle always returns at the exact same place, when the cartridge is moved back form the second position into the first position. Moreover the self-centering structure represents an upstream support for the cartridge which is otherwise only supported at its downstream end. Thus the reliability of the attachment of the cartridge is increased. Finally, the conical contact faces between the release end of the nozzle and the self-centering structure provide improved sealing capabilities such that when the cartridge is in the first position liquid is efficiently prevented from leaking out of the cartridge.

The exact dimensions of the conical self-centering structure may vary depending on the viscosity of the liquid and the related capillarity. The width of the gap that is created when the cartridge is moved in the second position is adjusted such that the desired flow of liquid onto the heater element is achieved.

The self-centering structure can be fixed onto the heater element. In a preferred embodiment the heater element extends around the self-centering structure and both elements are fixed to the distal wall of the aerosol forming chamber.

The self centering-structure may comprise a release pin and the nozzle of the cartridge is slideably seated on the release pin. Upon movement of the cartridge from the first position into the second position the nozzle slides along the release pin from a closing position to a release position. Preferably, the nozzle has release end with generally cylindrical shape and the release pin has a cylindrical shape that corresponds to the inner cross-section of the release end of the nozzle. The release pin may have head portion and a base portion. The release pin may have a central portion with reduced diameter which is in fluid connection with the liquid storage portion when the cartridge is in the first position. Fluid connection with the liquid storage portion is preferably totally interrupted when the cartridge is in second position. In this way a predefined portion of the liquid is trapped in the recessed area when the cartridge is in the first position. When the user draws a puff and the cartridge is moved in the second position the liquid comprised between the recessed portion of the release pin and the nozzle is dispensed through the release end onto the heater, while further delivery of liquid is prevented by the cylindrical head portion of the release pin blocking the flow of additional liquid through the nozzle. The amount of liquid to be dispensed is proportioned by the fluid trapped in the recessed area and only the well-defined amount of liquid is then dispensed on the heater when a user draws a puff at the system. The base portion of the release pin again may comprise a conical part for improving sealing of the nozzle.

In a further preferred embodiment the aerosol-generating system comprises an actuation means for forcing the plunger into the cartridge. The activation means is preferably activated upon movement of the cartridge within the housing of the system.

The actuation means may comprise a coupling element that is sealingly coupled to the cartridge. The coupling mechanism between the coupling element and the cartridge is preferably Luer-lock-type coupling mechanism. Such Luer-lock connections are well known from medical applications. The two parts to be connected comprise conical contact surfaces that form a hermetic seal. In order to prevent accidental decoupling, the coupling mechanism comprises a threaded or partly threaded portion such that the cartridge can be secured e.g. by a partial turn, preferably only a ¼ turn. Any other suitable coupling mechanisms known to the person skilled in the art may be employed.

The coupling element may have a similar cross-section as the cartridge and may be of general cylindrical shape. It preferably comprises a membrane at its downstream end and defines a pressure chamber between the membrane and the plunger. The membrane is pushed inwardly, i.e. towards the plunger, upon movement of the cartridge from the first position to the second position. Preferably there is provided a stationary element that is fixed to the housing just downstream from the membrane. Upon movement of the cartridge from the first into the second position the membrane is pushed against the stationary element, such that the membrane is pressed inwardly towards the plunger. By pressing the membrane, the pressure within the pressure chamber defined by the coupling element is increased and the plunger is moved in the cartridge towards the nozzle. Movement of the plunger leads to dispense of liquid through the nozzle. In this moment the cartridge is in the second position, i.e. there is already a gap created between the nozzle and the heater element or the distal wall of the aerosol forming chamber such that the liquid can exit from the nozzle and be dispensed onto the heater element for vaporization.

The stationary element against which the membrane is pressed may have any suitable shaped and is preferably located in a centrally aligned position with respect to the membrane. For example the stationary element may be a pin having generally cylindrical or truncated conical shape.

In order to allow the membrane to return to its initial shape, a one way air valve is preferably provided in a wall of the coupling element or the pressure chamber. Ambient air is allowed to enter into the pressure chamber via the one way valve, directly after the puff when the cartridge returns into the first position and the pressure from the stationary element on the membrane is released.

In a further aspect, the present invention is directed to a method for manufacturing an aerosol-generating system, comprising the steps of providing a housing with an air inlet and an air outlet defining an air flow path, and providing a heater element that is placed inside the housing, preferably on a distal wall portion of the aerosol forming chamber that is located in the air flow path. The method further comprises the steps of providing a cartridge and moveably mounting the cartridge in the housing such that the cartridge is reversibly displaceable from a first position into a second position. The cartridge comprises a liquid storage portion for holding an aerosol-generating liquid, and has an opening for delivery of the aerosol-generating liquid, the cartridge further comprising a plunger, moveably mounted in the cartridge. When an airstream is created between the air inlet and the air outlet, the cartridge is moved by the airstream within the housing and the movement of the cartridge activates release of a portion of the aerosol-generating liquid through the opening of the cartridge.

In a further aspect, the present invention is directed to a cartridge suitable to be used in an aerosol generating device. The cartridge comprises a liquid storage portion for holding an aerosol-generating liquid and has an opening for delivery of the aerosol-generating liquid. The cartridge further comprises a moveable plunger The heater element may be a metallic or ceramic heater element that is electrically operated. The heater element may comprise a mesh or array of filaments allowing for a greater area of the heater to be in contact with a liquid being vapourised. The heater assembly can be inexpensively produced, using readily available materials and using mass production techniques. The heater assembly can be robust allowing it to be handled and fixed to other parts of the aerosol-generating system during manufacture, and in particular to form part of a removable cartridge. The provision of electrically conductive contact portions forming part of the heater element allows for reliable and simple connection of the heater assembly to a power supply.

The heater element may be substantially flat. As used herein, "substantially flat" means formed in a single plane and not wrapped around or other conformed to fit a curved or other non-planar shape. A flat heater assembly can be easily handled during manufacture and provides for a robust construction. Further a flat heater element provides a defined contact surface, such that when the nozzle is directly pressed on the flat surface of the heater release of liquid can be prevented.

The heater assembly may comprise at least one filament made from a first material and at least one filament made from a second material different from the first material. This may be beneficial for electrical or mechanical reasons. For example, one or more of the filaments may be formed from a material having a resistance that varies significantly with temperature, such as an iron aluminum alloy, stainless steel alloys, carbon fiber filaments, or a combination of those. It is preferred that the resistive heating filaments are made of materials complying with applicable toxicology regulations for heating elements at the operating temperatures. This allows a measure of resistance of the filaments to be used to determine temperature or changes in temperature. This can be used in a puff detection system and for controlling heater temperature to keep it within a desired temperature range.

The heater element is preferably supported by the distal wall of an aerosol forming chamber manufactured from an electrically insulating material, preferably a material that is able to tolerate high temperatures (in excess of 300 degree Celsius) and rapid temperature changes. An example of a suitable material is a polyimide film, such as Kapton® or laminated fluorinated ethylene propylene, (FEP).

The heater element may also be made of a disc of non-conductive material, such as ceramic or silicon, as substrate and the electrical resistance element may be deposited, printed or deposited with a specific given geometry and thickness for the specific purpose The surface that will be in contact with the liquid to produce the aerosol may be coated with a thin layer of glass or vitro-ceramic, which also mechanically protects the electrical resistance and isolates avoiding direct contact of the liquid with the electrical resistance materials.

The aerosol-forming substrate is a substrate capable of releasing volatile compounds that can form an aerosol. The volatile compounds may be released by heating the aerosol-forming substrate.

The aerosol-forming substrate may comprise plant-based material. The aerosol-forming substrate may comprise tobacco. The aerosol-forming substrate may comprise a tobacco-originating material containing volatile tobacco flavour compounds, which are released from the aerosol-forming substrate upon heating. The aerosol-forming substrate may alternatively comprise a non-tobacco-originating material. The aerosol-forming substrate may comprise homogenized plant-based material. The aerosol-forming substrate may comprise homogenised tobacco material. The aerosol-forming substrate may comprise at least one aerosol-former. An aerosol-former is any suitable known compound or mixture of compounds that, in use, facilitates formation of a dense and stable aerosol and that is substantially resistant to thermal degradation at the operating temperature of operation of the system. Suitable aerosol-formers are well known in the art and include, but are not limited to: polyhydric alcohols, such as triethylene glycol, 1,3-butanediol and glycerine; esters of polyhydric alcohols, such as glycerol mono-, di- or triacetate; and aliphatic esters of mono-, di- or polycarboxylic acids, such as dimethyl dodecanedioate and dimethyl tetradecanedioate. Preferred aerosol formers are polyhydric alcohols or mixtures thereof, such as triethylene glycol, 1,3-butanediol and, most preferred, glycerine. The aerosol-forming substrate may comprise other additives and ingredients,.

The aerosol-generating liquid preferably comprises nicotine. The aerosol-generating liquid preferably comprises from 0.1% to 10% by weight, preferably from 0.2% to 5%, preferably from 0.5% to 2% by weight of nicotine.

The aerosol-generating liquid may comprise glycerol. The aerosol-generating liquid may comprise from 20% to 80% or from 50% to 70% by weight of glycerol.

The aerosol-generating liquid may comprise water, preferably from 5% to 20% by weight of water, for example from 8% to 15% by weight of water.

The aerosol-generating liquid may comprise propylene glycol, preferably from 5% to 50% by weight of propylene glycol, for example from 10% to 40% by weight of propylene glycol.

The aerosol-generating liquid may comprise flavour, preferably from 0.1% to 5% by weight of flavour, for example from 0.5% to 3% by weight of flavour.

The system may further comprise electric circuitry connected to the heater element and to an electrical power source, the electric circuitry configured to monitor the electrical resistance of the heater element or of one or more filaments of the heater element, and to control the supply of power to the heater element from the power source dependent on the electrical resistance of the heater element or specifically the electrical resistance of the one or more filaments.

The electric circuitry may comprise a microprocessor, which may be a programmable microprocessor, a microcontroller, or an application specific integrated chip (ASIC) or other electronic circuitry capable of providing control. The electric circuitry may comprise further electronic components. The electric circuitry may be configured to regulate a supply of power to the heater. Power may be supplied to the heater element continuously following activation of the system or may be supplied intermittently, such as on a puff by puff basis. The power may be supplied to the heater element in the form of pulses of electrical current.

The system advantageously comprises a power supply, typically a battery such as a lithium iron phosphate battery, within the main body of the housing. As an alternative, the power supply may be another form of charge storage device such as a capacitor. The power supply may require recharging and may have a capacity that allows for the storage of enough energy for one or more experiences. For example, the power supply may have sufficient capacity to allow for the continuous generation of aerosol for a period of around six minutes, corresponding to the typical time taken to smoke a conventional cigarette, or for a period that is a multiple of six minutes. In another example, the power supply may have sufficient capacity to allow for a predetermined number of puffs or discrete activations of the heater.

The system may comprise a main unit and a cartridge that is removably coupled to the main unit, wherein the liquid storage portion is provided in the cartridge and the main unit comprises the heater assembly and the power supply. The heater element may be removably coupled to the main unit such that the heater element can be replaced in regular intervals. As used herein, the expression "removably coupled" means that the corresponding elements can be coupled and uncoupled from the system without significantly damaging either the elements or the system.

The system may be an electrically operated aerosol-generating system. The system may be a handheld aerosol-generating system. The aerosol-generating system may have a size comparable to a conventional cigar or cigarette. The aerosol-generating system may have a total length between approximately 30 mm and approximately 150 mm. The aerosol-generating system may have an external diameter between approximately 5 mm and approximately 30 mm.

Embodiments of the invention will now be described, by way of example only, with reference to the accompanying drawings, in which.

Figure 1:
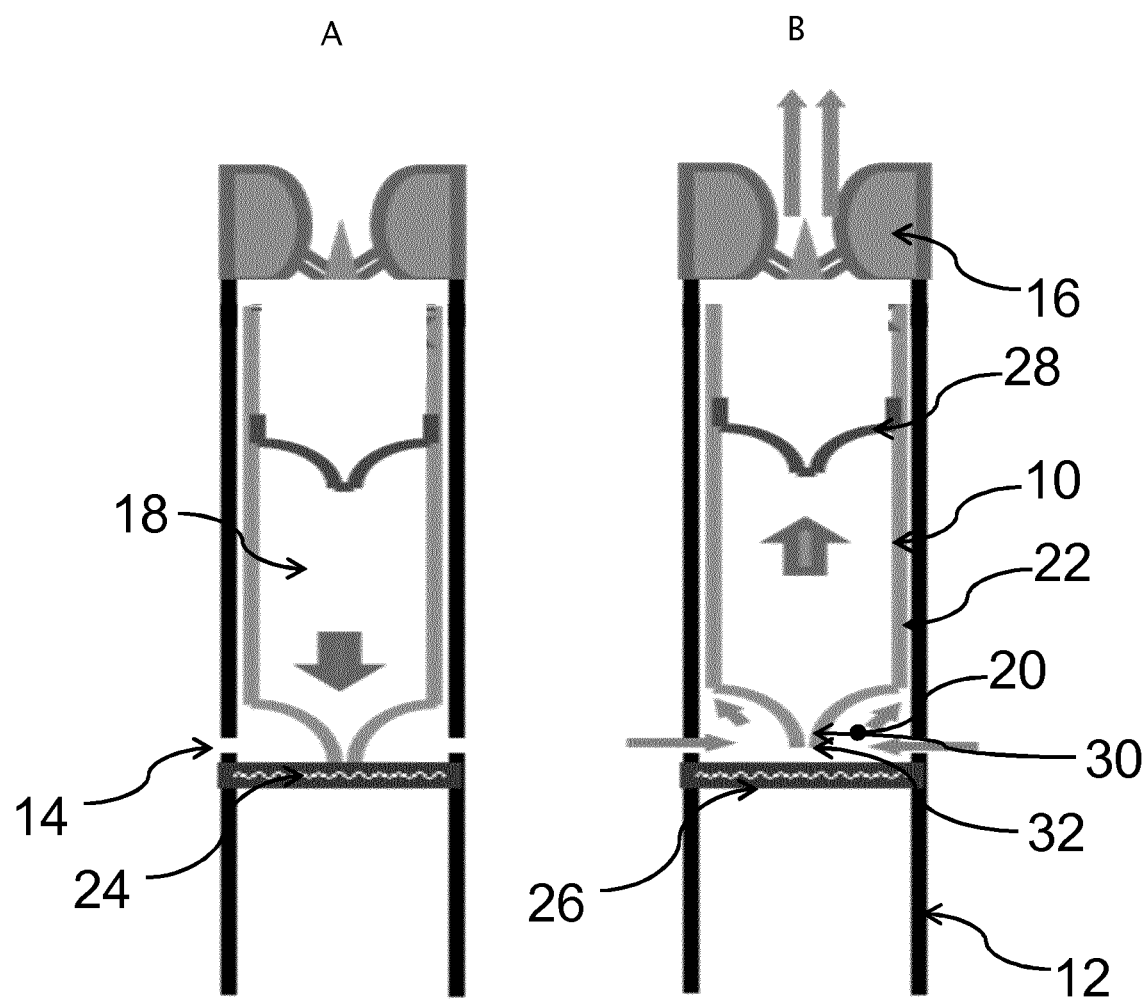
FIGS. 1a and 1b are schematic illustrations of a system, incorporating a moveable cartridge, in accordance with an embodiment of the invention.

FIGS. 1a and 1b show schematic illustrations of an aerosol generating system incorporating a moveable cartridge 10 that contains aerosol-generating liquid. In FIGS. 1a and 1b the aerosol-generating system is an electronic cigarette comprising a housing 12 with air inlets 14 and a mouthpiece 16 representing an air outlet. Between air inlets 14 and the mouthpiece 16 an air flow path 18 is defined. The air flow path directs the air flow from the air inlets 14 via an aerosol forming chamber 20, through a circular gap 22 between the cartridge 10 and the inner surface of the housing 12 to the mouthpiece 16. A heater element 24 is provided at the distal wall 26 of the aerosol forming chamber. The cartridge 10 comprises a moveably mounted plunger 28 and a nozzle 30 with a release end 32 for dispensing liquid from the liquid storage portion 18 in the interior of the cartridge 10 onto the heater element 24. The liquid storage portion 18 corresponds to the volume of the cartridge 10 between the plunger 28 and the release end 32 of the nozzle 30. Because the plunger 28 is moveable, the volume of the liquid storage portion 18 is variable. In a first position of the cartridge 10, the cartridge 10 abuts the heater element 24 such that no liquid can be dispensed.

When the user draws a puff at the mouthpiece 16 of the electronic cigarette, an air stream is created between the air inlets 14 and the mouthpiece 16. This air stream contours the cartridge 10 and moves the cartridge 10 into a second position shown in FIG. 1b in which a gap 46 is created between the release end 32 of the nozzle 30 of the cartridge 10 and the heater element 24. During the puff, a drop of liquid is dispensed onto the heater element 24. The liquid is vaporized on the heater element 24 and the resulting vapor is mixed with the air stream to form an aerosol that is delivered along the air stream path towards the mouthpiece 16 of the e-cigarette and is inhaled by the consumer. After puffing and when the air stream ceases, the cartridge 10 will return to the first position such that no more liquid is dispensed. As the liquid is dispensed the moveable plunger 28 will move towards the release end 32 of the cartridge 10 such that the volume of the liquid storage portion 18 of the cartridge 10 will gradually decrease.

Figure 2:
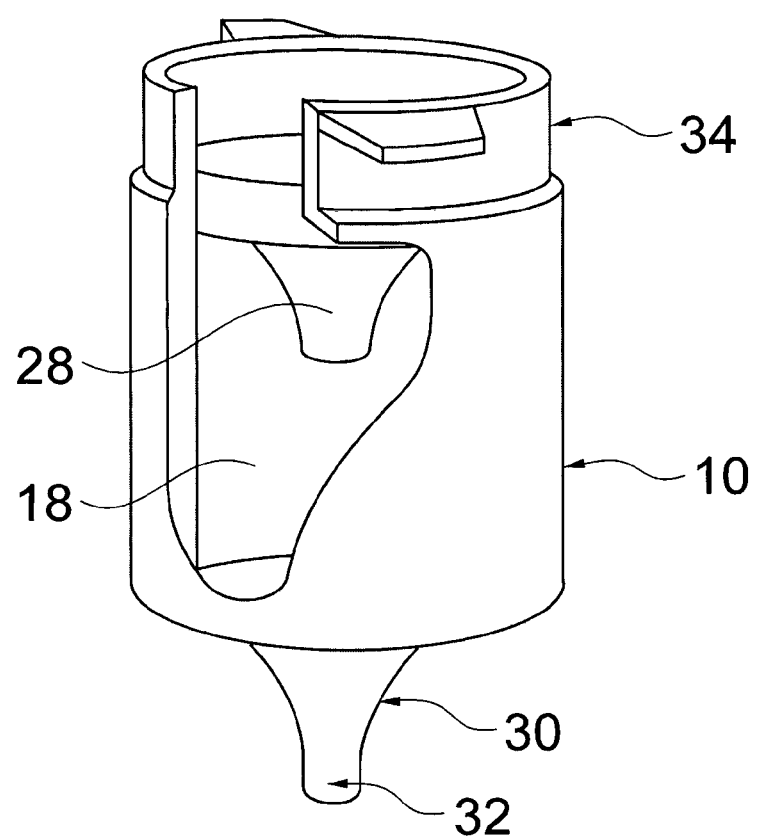
FIG. 2 is an enlarge view of the moveable cartridge including a moveable plunger.

FIG. 2 shows an enlarged view of a cartridge 10 suitable for use in the system of FIG. 1. The cartridge 10 comprises a nozzle 30 with a release end 32. Within the cartridge 10 a plunger 28 is moveably mounted. The shape of the plunger 28 corresponds to the shape of the nozzle 30 such that the complete content of the cartridge 10 can be released, when the plunger 28 is moved to the lowermost position. The cartridge 10 is of generally cylindrical shape. At the top end of the cartridge 10 an attachment means 34 is provided with which the cartridge 10 may be connected to a corresponding receiving portion (not shown) at the inside of the housing of the electronic cigarette. In this case the attachment means is a Luer-lock type connection.

Figure 3:
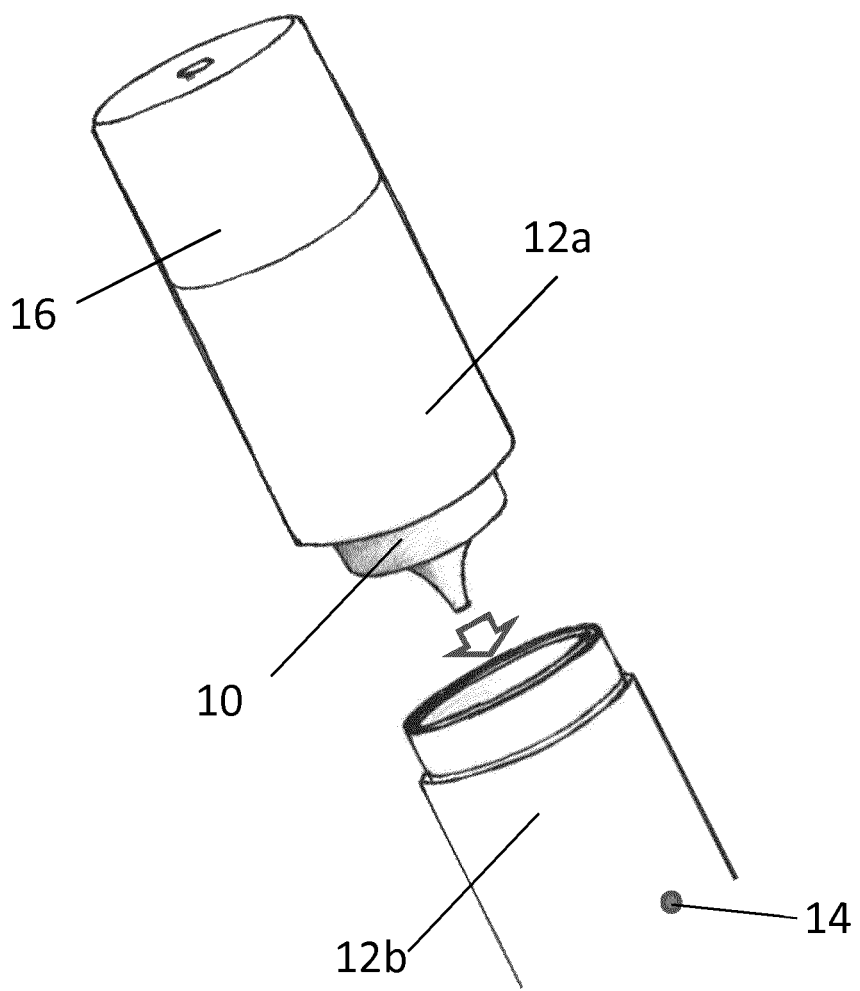
FIG. 3 is an exploded view of the aerosol generating system including the cartridge of FIG. 2.

FIG. 3 is an exploded view of an electronic cigarette including the cartridge 10 of FIG. 2. The electronic cigarette comprises a first housing part 12a with an air inlet 14 as well as a power source and electric circuitry (not shown) for providing electrical power to the heater element. The cartridge 10 is inserted and fixed to a second part 12b of the housing comprising the mouthpiece 14. The second part 12b of the housing is connectable to the first part 12a of the housing.

Figure 4:
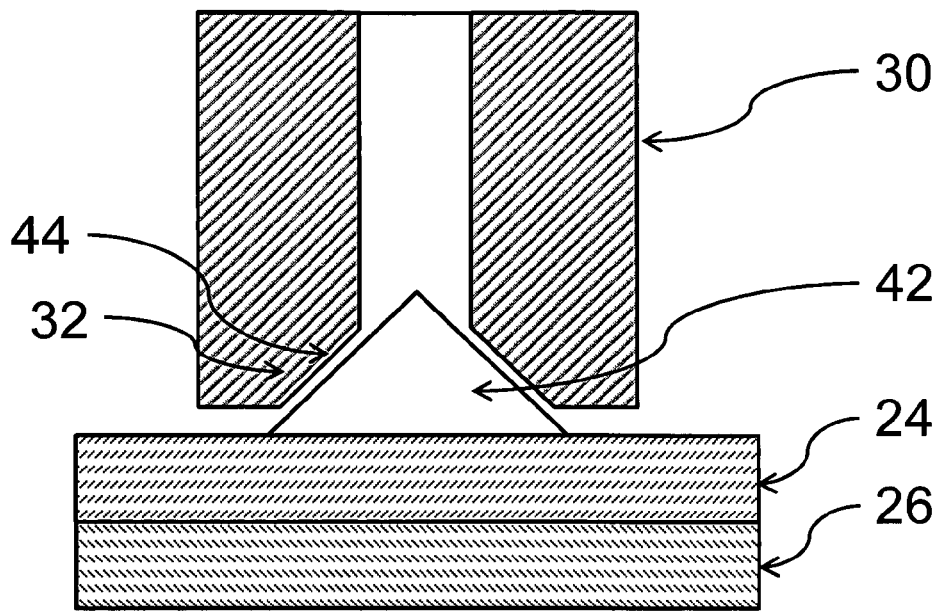
FIG. 4 is an enlarged view showing the release end of the nozzle when seated on a self-centering structure.

In FIG. 4 an enlarged view of the release end 32 of the nozzle 30 when seated on a self-centering structure is depicted. The distal wall 26 of the aerosol forming chamber 20 supports a heater element 24. In the center of the heater element 24 a conical structure 42 is provided. The conical structure 42 is located such that the release end 32 of the nozzle 30 of the cartridge 10 is seated thereon, when the cartridge 10 is in the first position. In the first position the conical structure 42 prevents liquid from being dispensed from the cartridge 10. In order to improve the sealing properties of the contact area between the conical element 42 and the nozzle 30, the release end 32 of the nozzle 30 comprises a chamfer 44 having an angle that corresponds to the angle of the surface of the conical structure 42. The conical structure 42 also represents a self-centering structure for the cartridge 10 and ensures correct and reproducible positioning of the nozzle 30 when the cartridge 10 is in the first position.

Figure 5:
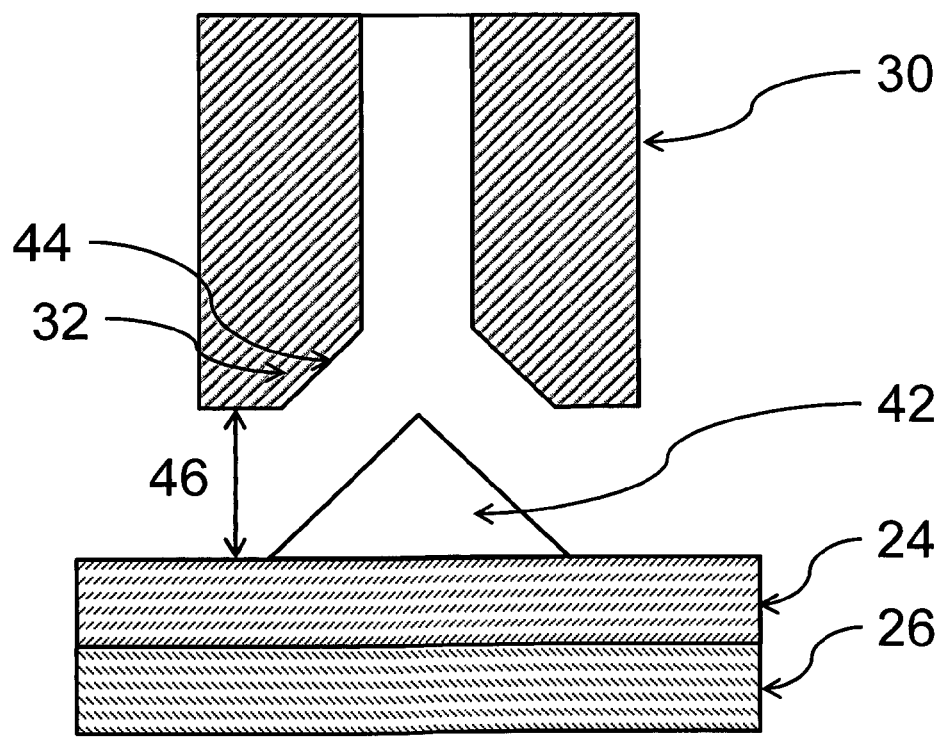
FIG. 5 is showing the structure of FIG. 4 in which the moveable cartridge is in the second position.

When a puff is drawn at the electronic cigarette, the cartridge 10 is moved in the second position in which a gap 46 is created between the nozzle 30 and the heater element 24 and the conical structure 42, respectively. This situation is depicted in FIG. 5. In this embodiment the cartridge is moved by about 1 mm such that only a small portion of only 1 to 4 mg of liquid, more preferably 2 to 3 mg of liquid, is dispensed from the cartridge 10 per puff.

Figure 6:
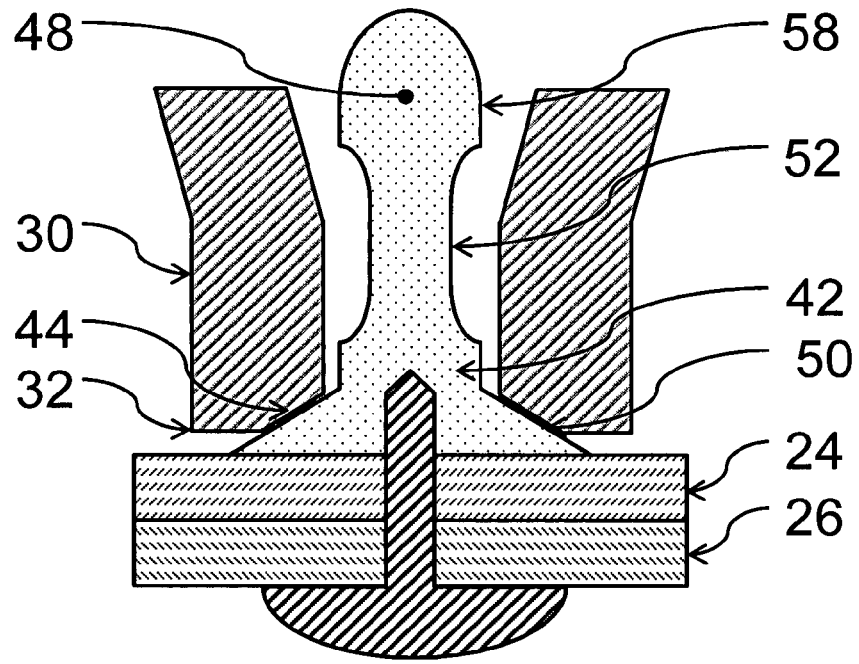
FIG. 6 illustrates a modification of the structure of FIG. 4, in which the self-centering structure comprises a release pin.
Figure 8:
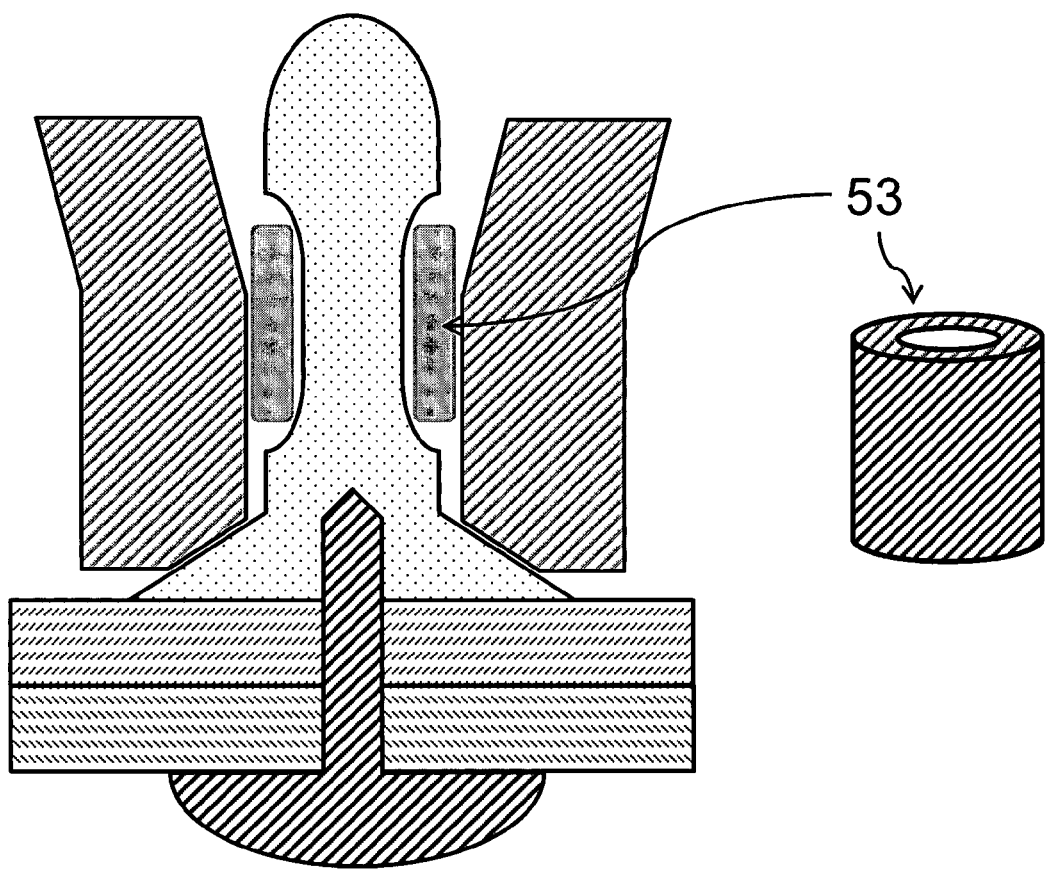
FIG. 8 illustrates the predefined amount of liquid trapped in the recess portion of the release pin.

FIG. 6 shows a further embodiment of the present invention which allows for even more precise dosage of the liquid to be dispensed per puff. To this end the self-centering conical structure 42 further comprises a generally cylindrical release pin 48 having a cross-section that corresponds to the generally cylindrical cross-section of the nozzle 30 of the cartridge 10. When the cartridge 10 is in the first position, as depicted in FIG. 6, the release pin 48 fully extends into the nozzle 30 and the chamfer 44 at the release end 32 of the nozzle 30 abuts the conical portion 50 at the base of the release pin 48. The release pin 48 comprises an intermediate recessed portion 52 with reduced diameter. When the cartridge 10 is in the first position, the recessed area 52 is in fluid communication with the liquid storage portion 18 of the cartridge 10 and is therefore filled with liquid. This situation is illustrated in FIG. 8. The portion 53 of liquid comprised in the recessed area 52 determines the amount of liquid dispensed during a puff to the heater assembly 24.

Figure 7:
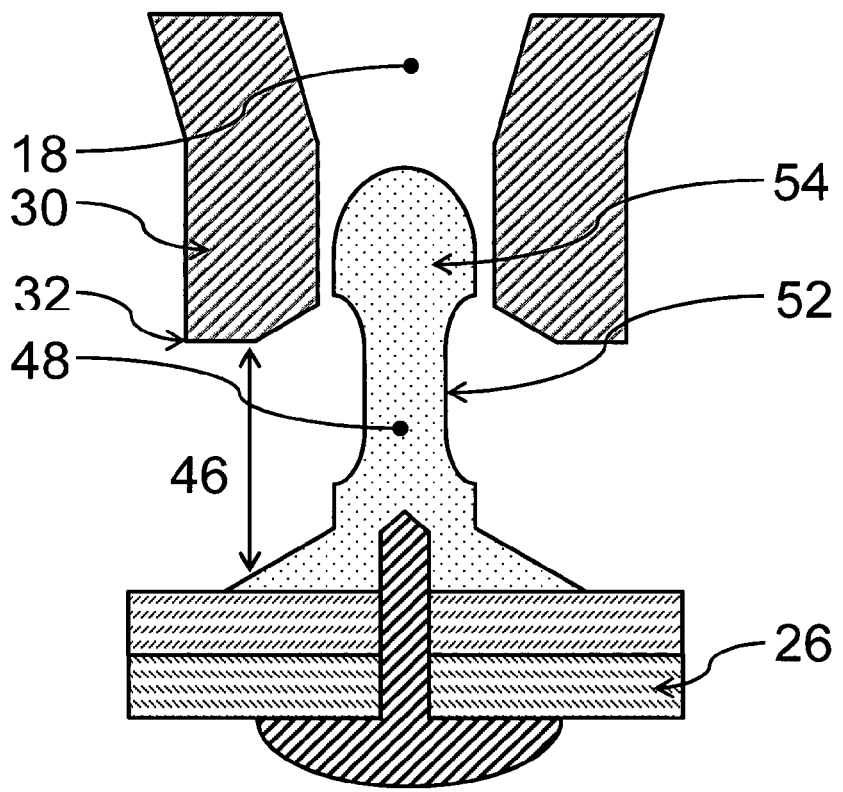
FIG. 7 shows the structure of FIG. 6 in which the moveable cartridge is in the second position.

FIG. 8 illustrates the structure of FIG. 7 wherein the cartridge is in the second position. When the cartridge 10 is moved into the second position the nozzle 30 slides along the release pin 48 in a direction away from the distal end 26 of the aerosol forming chamber 20, such that again a gap 46 is created between the release end 32 of the nozzle 30 and the base portion 50 of the release pin 48. During movement of the cartridge 10, the cylindrical head portion 58 of the release pin 48 comes into contact with the cylindrical portion of the nozzle 30 and thereby disconnects the recessed area 52 of the release pin 48 from the liquid storage portion 18 of the cartridge 10. When the cartridge 10 reaches the second position, the portion 53 of liquid trapped in the recessed area 52 is dispensed on the heater element 24. The cylindrical head portion 58 of the release pin 48 provides a closure for the nozzle 30 and therefore prevents dispense of additional liquid from the cartridge 10. In order to avoid occurrence of underpressure upon continued dispense of liquid from the cartridge 10, which underpressure might hamper further dispense of the liquid, the plunger 28 is moveably mounted in the cartridge 10 and moves toward the nozzle 30 of the cartridge 10 thereby reducing the volume of the liquid storage portion 18.

Figure 9:
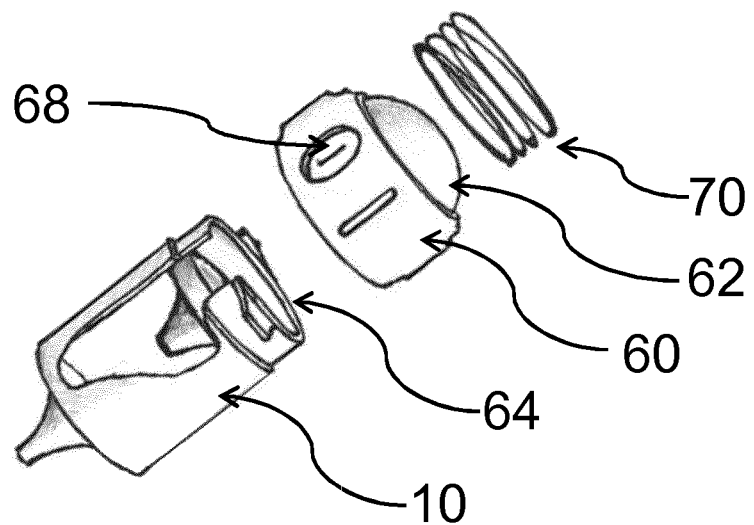
FIG. 9 is a detail view of an aerosol-generating system including actuation means for moving the plunger just before puffing.
Figure 10:
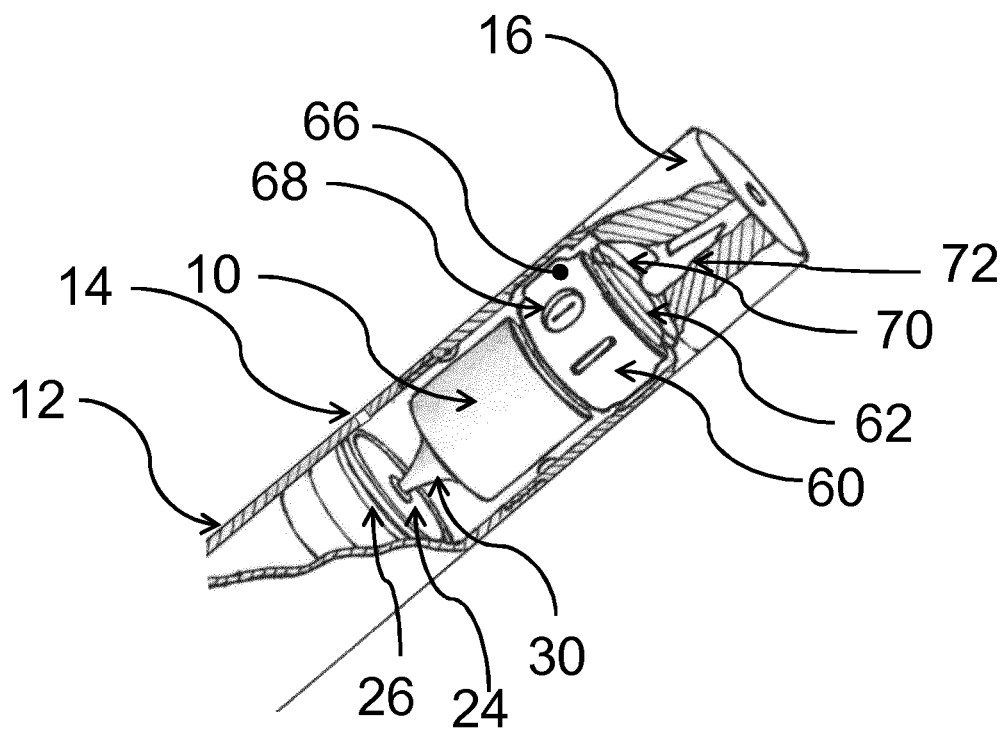
FIG. 10 illustrates the system of FIG. 9 at the start of the puff.

In FIGS. 9 to 12 a further embodiment of the present invention comprising actuation means for forcing the plunger 28 into the cartridge 10 is illustrated. The main elements of the actuation means are depicted in FIG. 9. The cartridge 10 depicted in FIG. 9 corresponds to the cartridge of FIG. 2. With the Luer-lock type coupling mechanism 64 the cartridge 10 is sealingly connected to a coupling element 60. The coupling element 60 has generally cylindrical shape and exhibits a flexible membrane 62 at the downstream end face. The coupling element 60 defines a pressure chamber 66 between the moveable plunger 28 of the cartridge 10 and the flexible membrane 62. A one-way valve 68 is provided in a sidewall of the coupling element 60 to allow for air flow into the pressure chamber 66, but to prevent air flow out of the pressure chamber 66. A resilient pressure spring 70 is provided between the mouthpiece 14 and the coupling element 60 such that the nozzle 30 of the cartridge 10 is pressed against the heater element 24 supported by the distal wall 26 of the aerosol forming chamber 20. In close relationship to the flexible membrane 62 a stationary pin 72 is provided centrally within the housing 12.

Figure 11:
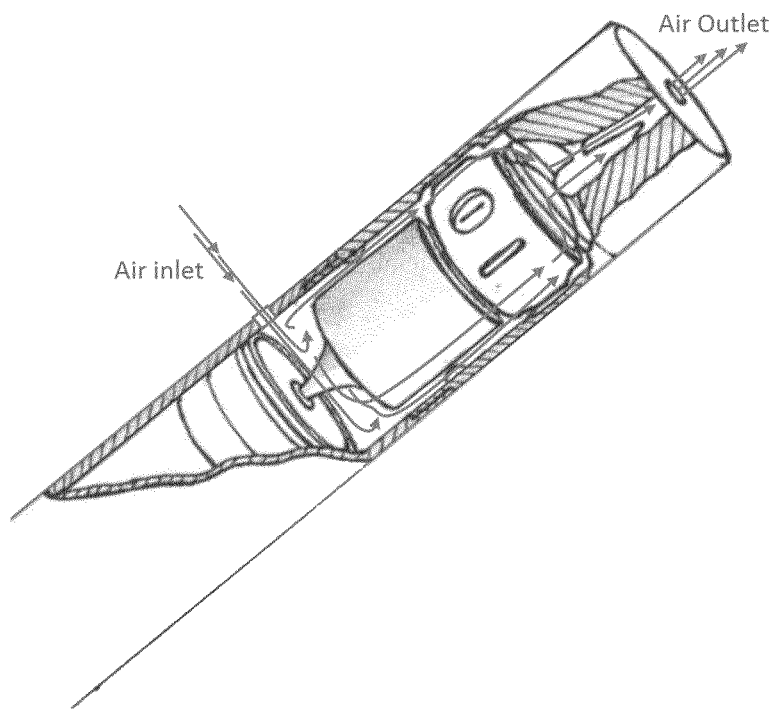
FIG. 11 illustrates the system of FIG. 9 during the puff.

As illustrated by the arrows indicated in FIG. 11, an air flow path is established between the air inlet 14 via the aerosol forming chamber 20, contouring the cartridge 10 and the coupling element 60 towards the mouthpiece 16 when a user draws a puff at the mouthpiece 16 of the electronic cigarette.

Figure 12:
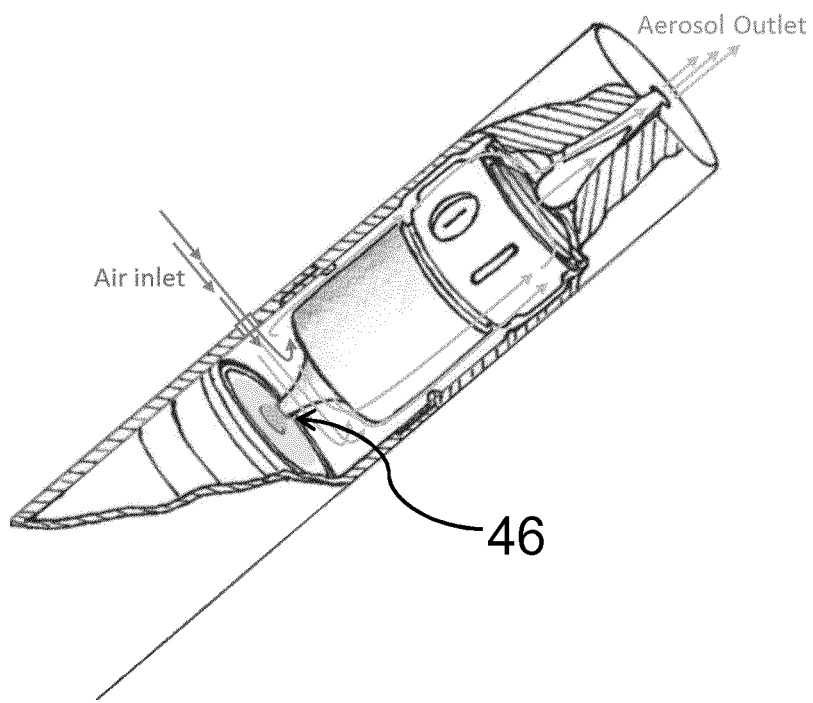
FIG. 12 illustrates the system of FIG. 9 just after puffing.

Due to the air flow during a puff the cartridge 10 together with the coupling element 60 is moved downstream towards the mouthpiece end of the electronic cigarette, as indicated in FIG. 12. Again a gap 46 is created between the nozzle 30 and the heater element 24. At the same time the flexible membrane 62 is pressed against the stationary pin 72 such that the pressure in the pressure chamber 66 is increased. The increased pressure forces the plunger 28 to move towards the nozzle 30, until pressure equilibrium is reached. Upon moving forward, the plunger 28 presses a portion of the liquid comprised in the liquid storage portion 18 of the cartridge 10 out of the nozzle 30 and the portion of liquid is released onto the heater 24.

After the puff, the pressure spring 70 forces the cartridge 10 back into the first position such that the nozzle 30 is again firmly pressed on the heater element 24 and further dispense of liquid is prevented. This corresponds to the situation shown in FIG. 10. The flexible membrane 62 also returns into its initial relaxed and expanded state. During return of the membrane 62 into its initial state, air is introduced into the pressure chamber 66 via the one-way valve 68. The amount of liquid dispensed during a single puff is determined inter alia from the movement of the cartridge 10, the pressure applied to the flexible membrane 62 and the pressure created in the pressure chamber 66 during a puff. The resistance to draw is adjustable by selection of the gap between the cartridge 10 and the housing 12 and by the spring rate of the pressure spring 70 used.

The invention claimed is:

1. An aerosol-generating system, comprising:
   a housing comprising an air inlet and an air outlet defining an air flow path therebetween;
   a heater element; and
   a cartridge moveably mounted in the housing and reversibly displaceable from a first position to a second position, the cartridge comprising a moveable plunger, a liquid storage portion configured to hold an aerosol-generating liquid, and an opening configured to deliver the aerosol-generating liquid,
   wherein the cartridge is further configured to activate release of a portion of the aerosol-generating liquid through the opening, when the cartridge is moved by an airstream created between the air inlet and the air outlet within the housing.

2. The aerosol-generating system according to claim 1, wherein the cartridge is a polymeric material.

3. The aerosol-generating system according to claim 1, wherein the opening is a funnel-shaped opening.

4. The aerosol-generating system according to claim 3, wherein the plunger has a shape that corresponds to the funnel-shaped opening of the cartridge.

5. The aerosol-generating system according to claim 1, further comprising a resilient element configured to bias the cartridge in the first position.

6. The aerosol-generating system according to claim 5, wherein the resilient element is a compression spring disposed between an outlet end of the housing and a pressure chamber.

7. The aerosol-generating system according to claim 1, wherein the heater element is provided at a distal end of an aerosol forming chamber.

8. The aerosol-generating system according to claim 1, further comprising a resilient element configured to bias the cartridge in the first position, such that the opening of the cartridge is pressed against the heater element.

9. The aerosol-generating system according to claim 1, further comprising a self-centering structure disposed at a distal end of an aerosol forming chamber or on the heater element.

10. The aerosol-generating system according to claim 9, wherein the cartridge further comprises a nozzle, wherein the self-centering structure includes a conical portion, and wherein the nozzle of the cartridge is seated on the self-centering structure when the cartridge is in the first position.

11. The aerosol-generating system according to claim 10, wherein the self-centering structure comprises a release pin, the nozzle of the cartridge being slideably seated on the release pin and being configured to slide along the release pin from a closing position to a release position upon movement of the cartridge from the first position into the second position.

12. The aerosol-generating system according to claim 11, wherein the nozzle includes a release end having a cylindrical shape, the release pin having a cylindrical shape that corresponds to an inner cross-section of the release end of the nozzle, and wherein a central part of the release pin has an area with reduced diameter relative to another part of the release pin.

13. The aerosol-generating system according to claim 1, further comprising actuation means for forcing the moveable plunger into the cartridge.

14. The aerosol-generating system according to claim 13, wherein the actuation means comprises a coupling element that is sealingly coupled to the cartridge, wherein the coupling element comprises a membrane and defines a pressure chamber between the membrane and the plunger, and wherein the membrane is configured to be pushed inwardly upon movement of the cartridge from the first position to the second position.

15. The aerosol-generating system according to claim 14, further comprising a stationary element against which the membrane is pressed upon movement of the cartridge from the first position to the second position, wherein a pressure in the pressure chamber is increased upon pressing of the membrane, such that the plunger is moved into the cartridge and the portion of the aerosol-generating liquid is dispensed through the opening of the cartridge.

16. A process of manufacture of an aerosol-generating system, comprising:

providing a housing comprising an air inlet and an air outlet defining an air flow path therebetween;

providing a heater element disposed inside the housing; and providing a cartridge and moveably mounting the cartridge in the housing such that the cartridge is reversibly displaceable from a first position to a second position, the cartridge comprising a moveable plunger, a liquid storage portion configured to hold an aerosol-generating liquid, and an opening configured to deliver the aerosol-generating liquid, wherein the cartridge is further configured to activate release of a portion of the aerosol-generating liquid through the opening, when the cartridge is moved by an airstream created between the air inlet and the air outlet within the housing.

* * * * *